United States Patent
Corbin, III et al.

(10) Patent No.: US 6,994,790 B2
(45) Date of Patent: Feb. 7, 2006

(54) WHOLE BLOOD COLLECTION AND PROCESSING METHOD

(75) Inventors: Frank Corbin, III, Littleton, CO (US); Steven Gage Urdahl, Superior, CO (US)

(73) Assignee: Gambro, Inc., Lakewood, CO (US)

( * ) Notice: Subject to any disclaimer, the term of this patent is extended or adjusted under 35 U.S.C. 154(b) by 256 days.

(21) Appl. No.: 10/358,381

(22) Filed: Feb. 3, 2003

(65) Prior Publication Data

US 2003/0146170 A1 Aug. 7, 2003

Related U.S. Application Data

(60) Provisional application No. 60/353,277, filed on Feb. 1, 2002.

(51) Int. Cl.
*B01D 61/16* (2006.01)

(52) U.S. Cl. .................. 210/639; 210/97; 210/101; 210/198.1; 210/321.6; 210/416.1; 210/651; 210/767; 604/6.03; 604/6.09; 604/406; 604/408

(58) Field of Classification Search .............. 210/85, 210/90, 97, 101, 103, 110, 198.1, 199, 206, 210/257.1, 257.2, 326.1, 406, 416.1, 639, 210/645, 650, 651, 739, 741, 767; 604/6.01, 604/6.03, 6.09, 65, 67, 403, 406, 408, 410

See application file for complete search history.

(56) References Cited

U.S. PATENT DOCUMENTS

| | | |
|---|---|---|
| 2,257,823 A | 10/1941 | Stokes |
| 2,328,569 A | 9/1943 | McGaw |
| 2,663,298 A | 12/1953 | Rose |

(Continued)

FOREIGN PATENT DOCUMENTS

| | | |
|---|---|---|
| DE | 1922917 | 11/1970 |
| EP | 0 578 086 | 6/1993 |
| EP | 0 591 980 B1 | 5/1994 |

(Continued)

OTHER PUBLICATIONS

Diepenhorst, P. et al., "Removal of leukocytes from whole blood and erythrocyte suspensions by filtration through cotton wool," (1975) *Vox Sang.* 29:15–22.

(Continued)

*Primary Examiner*—Joseph Drodge
(74) *Attorney, Agent, or Firm*—Greenlee, Winner and Sullivan, P.C.

(57) ABSTRACT

A method is disclosed for collecting and processing whole blood. Whole blood is collected at several remote donor sites and transported to a central blood-processing center, where information regarding demand for blood products is used to direct processing of whole blood into blood products. Whole blood is initially collected in collection bags unattached to satellite bags instead of commonly used multiple bag sets. When the determination is made at the blood processing center as to which blood products are to be made, the appropriate satellite bags and/or other system components are sterile docked to the blood-collection bag and the whole blood is processed. The use of blood-collection bags initially unattached to satellite bags eliminates waste and simplifies the transportation and processing of whole blood. Also disclosed are blood collection systems that remove leukocytes and collect whole blood into blood-collection bags unattached to satellite bags.

20 Claims, 7 Drawing Sheets

U.S. PATENT DOCUMENTS

| | | | |
|---|---|---|---|
| 2,702,034 A | 2/1955 | Walter | |
| 2,777,443 A | 1/1957 | Thomas et al. | |
| 2,838,046 A | 6/1958 | Butler | |
| 2,894,510 A | 7/1959 | Bellamy, Jr. | |
| 2,896,619 A | 7/1959 | Bellamy, Jr. | |
| 2,950,716 A | 8/1960 | Bellamy, Jr. et al. | |
| 3,110,308 A | 11/1963 | Bellamy, Jr. | |
| 3,185,154 A | 5/1965 | Caccavo et al. | |
| 3,187,750 A | 6/1965 | Tenczar, Jr. | |
| 3,209,752 A | 10/1965 | Bujan et al. | |
| 3,211,144 A | 10/1965 | Nehring et al. | |
| 3,221,741 A * | 12/1965 | Le Veen | 604/416 |
| 3,327,709 A | 6/1967 | Nehring et al. | |
| 3,448,041 A | 6/1969 | Swank | |
| 3,509,879 A | 5/1970 | Bathish et al. | |
| 3,788,374 A | 1/1974 | Saijo | |
| 3,870,042 A | 3/1975 | Viguier | |
| 3,892,236 A * | 7/1975 | Djerassi | 604/6.03 |
| 3,985,135 A | 10/1976 | Carpenter et al. | |
| 4,086,924 A * | 5/1978 | Latham, Jr. | 604/6.04 |
| 4,146,172 A | 3/1979 | Cullis et al. | 233/26 |
| 4,191,182 A | 3/1980 | Popovich et al. | |
| 4,223,675 A | 9/1980 | Williams | |
| 4,305,443 A | 12/1981 | Bayham | |
| 4,379,452 A | 4/1983 | DeVries | |
| 4,381,776 A * | 5/1983 | Latham, Jr. | 604/317 |
| 4,416,772 A | 11/1983 | Sato et al. | 210/137 |
| 4,439,192 A | 3/1984 | Leurink | 604/408 |
| 4,443,215 A * | 4/1984 | Smith | 604/29 |
| 4,447,191 A | 5/1984 | Bilstad et al. | 417/63 |
| 4,458,539 A | 7/1984 | Bilstad et al. | 73/861 |
| 4,464,167 A | 8/1984 | Schoendorfer et al. | |
| 4,481,827 A | 11/1984 | Bilstad et al. | 73/861 |
| 4,498,983 A | 2/1985 | Bilstad et al. | 210/97 |
| 4,507,119 A * | 3/1985 | Spencer | 156/152 |
| 4,526,515 A | 7/1985 | DeVries | 417/63 |
| 4,605,503 A | 8/1986 | Bilstad et al. | 210/651 |
| 4,608,178 A | 8/1986 | Johansson et al. | 210/744 |
| 4,637,813 A | 1/1987 | DeVries | |
| 4,648,866 A | 3/1987 | Malbrancq et al. | |
| 4,655,742 A | 4/1987 | Vantard | |
| 4,664,659 A | 5/1987 | Shinohara | 604/283 |
| 4,680,025 A | 7/1987 | Kruger et al. | |
| 4,687,580 A | 8/1987 | Malbrancq et al. | 210/651 |
| 4,731,053 A | 3/1988 | Hoffman | 604/89 |
| 4,767,541 A | 8/1988 | Wisdom | 210/749 |
| 4,786,286 A | 11/1988 | Cerny et al. | 604/406 |
| 4,806,252 A | 2/1989 | Brown et al. | 210/744 |
| 4,810,378 A | 3/1989 | Carmen et al. | 210/206 |
| 4,895,558 A * | 1/1990 | Cham | 604/5.03 |
| 4,898,573 A | 2/1990 | Takenaka et al. | 604/6 |
| 4,915,848 A | 4/1990 | Carmen et al. | 210/749 |
| 4,919,823 A | 4/1990 | Wisdom | 210/749 |
| 4,923,449 A * | 5/1990 | Toya et al. | 604/245 |
| 4,925,572 A | 5/1990 | Pall | 210/767 |
| 4,985,153 A * | 1/1991 | Kuroda et al. | 210/782 |
| 4,990,132 A | 2/1991 | Unger et al. | |
| 5,035,865 A | 7/1991 | Inaba et al. | 422/99 |
| 5,057,074 A | 10/1991 | Suzuki et al. | |
| 5,092,996 A | 3/1992 | Spielberg | 210/232 |
| 5,104,788 A | 4/1992 | Carmen, Raleigh A. et al. | 435/2 |
| 5,112,298 A | 5/1992 | Prince et al. | |
| 5,114,396 A | 5/1992 | Unger et al. | 494/37 |
| 5,167,656 A | 12/1992 | Lynn | 604/409 |
| 5,188,588 A | 2/1993 | Schoendorfer et al. | |
| 5,364,526 A | 11/1994 | Matkovich et al. | 210/206 |
| 5,403,272 A | 4/1995 | Deniega et al. | |
| 5,494,592 A | 2/1996 | Latham, Jr. et al. | 210/805 |
| 5,496,265 A | 3/1996 | Langley et al. | |
| 5,536,238 A | 7/1996 | Bischof | |
| 5,607,579 A | 3/1997 | Latham, Jr. et al. | 210/195.1 |
| 5,637,082 A * | 6/1997 | Pages et al. | 604/6.11 |
| 5,649,903 A | 7/1997 | Deniega et al. | |
| 5,795,317 A | 8/1998 | Brierton et al. | |
| 5,954,971 A | 9/1999 | Pages et al. | 210/739 |
| D440,300 S | 4/2001 | Högberg et al. | |
| 6,261,217 B1 | 7/2001 | Unger et al. | 494/45 |
| D446,855 S | 8/2001 | Högberg et al. | |
| 6,315,706 B1 | 11/2001 | Unger et al. | 494/23 |
| 6,325,750 B1 | 12/2001 | Jorgensen et al. | 494/21 |
| 6,328,726 B1 | 12/2001 | Ishida et al. | 604/408 |
| 6,348,031 B1 | 2/2002 | Unger et al. | 494/45 |
| 6,413,200 B1 | 7/2002 | Jorgensen et al. | 494/37 |
| 6,695,803 B1 * | 2/2004 | Robinson et al. | 604/4.01 |

FOREIGN PATENT DOCUMENTS

| | | |
|---|---|---|
| EP | 0 643 975 | 9/1994 |
| EP | 0 852 151 | 1/1998 |
| EP | 0 958 838 A3 | 11/1999 |
| EP | 0 958 838 A2 | 11/1999 |
| EP | 1 190 673 | 4/2001 |
| WO | WO93/18804 | 3/1993 |
| WO | WO 95/01842 | 1/1995 |
| WO | 99/59493 | 11/1999 |
| WO | WO 01/97943 | 6/2001 |
| WO | 03/026773 A1 | 4/2003 |

OTHER PUBLICATIONS

Diepenhorst, P. et al., "Removal of leukocytes from whole blood and erythrocyte suspensions by filtration through cotton wool," (1972) *Vox Sang.* 23:308–320.

Diepenhorst, P. et al., "Removal of leukocytes from whole blood and erythrocyte suspensions by filtration through cotton wool," (1972) *Vox Sang.* 23:321–330.

Diepenhorst, P. et al., "Removal of leukocytes from whole blood and erythrocyte suspensions by filtration through cotton wool," (1972) *Vox Sang.* 23:331–335.

Högman, C.F., *Leucocyte depletion of blood components*, VU University Press, Amsterdam, The Netherlands, 1994, Contents, pp. 1–3 and 52–57.

Kikugawa, K. and Minoshima, K., "Filter columns for preparation of leukocyte–poor blood for transfusion," (1978) *Vox Sang.* 34:281–290.

Lichtiger, B. et al., "Use of Imugard IG500 filters for preparation of leukocyte–poor blood for cancer patients," (1984) *Vox Sang.* 46:136–141.

Lovric, V.A. et al., "Filtered microaggregate–free erythrocyte concentrates with 35–day shelf life," (1981) *Vox Sang.* 41:6–10.

Reesink, H. W. et al., "Removal of leukocytes from blood by fibre filtration," (1982) *Vox Sang.* 42:281–288.

* cited by examiner

WHOLE BLOOD COLLECTION AND PROCESSING METHOD

CROSS REFERENCE TO RELATED APPLICATIONS

This application claims priority to U.S. Provisional Application No. 60/353,277 filed Feb. 1, 2002.

BACKGROUND OF THE INVENTION

This invention relates to improved manual and/or automatic whole blood collection and processing systems. It relates more particularly to methods and apparatus for simplifying volumetric whole blood collection and blood component processing and/or providing more control to one or more parts of whole blood processing.

In the United States, millions of units of donated whole blood are collected by blood banks each year. Whole blood is made up of red blood cells, white blood cells (also called leukocytes), and platelets, all suspended in a protein-containing fluid called plasma. Because patients are not likely to require each component of whole blood, most of the whole blood collected from donors is not stored and used for transfusion. Instead, the whole blood is separated into its clinically therapeutic components, red blood cells, platelets and plasma. The components are stored individually and used to treat a multiplicity of specific conditions.

Collection of whole blood can take place at community or hospital donation centers, but much blood collection takes place at remote sites, such as a church, business or school, during mobile blood drives. Typically, whole blood is collected from donors at a remote site, transported to a main processing blood center, processed into individual blood products and delivered to hospitals where the blood products are administered to patients.

Information, such as the time of collection, should be marked on the blood-collection bag. In addition, the blood type (A, B, AB, O, and the Rh factor) of collected blood needs to be known for subsequent transfusion into a patient with a compatible blood type. At the time of collection, the technician who collects blood from the donor will contemporaneously collect blood into connected tubing and vials. These blood samples will be used to screen for disease and determine blood type at the blood-processing center. Alternatively, other known methods such as use of an attached sample bulb can be used at the blood-processing center to process the samples for screening and typing. Bags should be marked with donor information. It is required by law that each blood product be traceable to the donor's test results, the donated unit of whole blood, the bag set in which the blood was collected, and the centrifuge used to process the blood, and other key aspects of the process.

In addition, demand for any given blood product will vary according to the needs of local hospitals and the difference in expiration times between each blood product. For example, red blood cells can be stored for up to forty-two days and plasma can be stored for up to one year. Platelets, however, can be stored for only up to five days. When blood is donated, there may be a great demand for one blood product but much less demand for another blood product.

Collecting and processing whole blood into needed blood products is a complex procedure. Whole blood should be processed or separated within eight hours of collection in the United States and twenty-four hours of collection in Europe, giving little time to screen and type blood samples, transport the collected blood to a processing center, determine what blood products should be processed from donated blood, and then execute the separation and storage process. A blood collection and separation system and method is therefore needed to provide greater flexibility, efficiency, and simplicity.

Currently whole blood is usually collected by gravity into a blood-collection bag containing anticoagulant. Pumps or vacuum may be used to facilitate blood flow. (See, e.g., U.S. Pat. No. 4,923,449.) Integrally manufactured with this collection bag are several attached satellite bags for receiving blood components following subsequent blood processing steps. Blood-collection bags and satellite bags are well known in the art.

The first blood-collection bags were typically single bags with a connected hollow tube and phlebotomy needle manufactured as part of the bag. Examples of single blood bags are illustrated or described in U.S. Pat. Nos. 2,896,619; 2,950,716; 3,788,374; and 4,664,659.

Attempts to access single blood bags for subsequent processing of the collected blood were problematic because of the introduction of potential contamination to the blood. The device commonly used today is formed as a series of three or four integrally connected plastic bags, including the collection bag and satellite bags, coupled to a tube with a hollow needle affixed to the end of the tube. (See U.S. Pat. Nos. 3,110,308; 4,223,675; 4,608,178; 4,919,823; and 5,104,788.) These multiple bag sets, commonly known as triple-packs and quad-packs, are sterilized during the manufacturing process to form a sterile closed system.

There are disadvantages with using multiple bag sets. It is often not necessary to separate each blood component for which a bag is provided because demand for that blood product may be low. In such situations, it is unnecessary and wasteful to provide the corresponding satellite bag in the multiple bag set used for blood collection. For example, if plasma is the only component to be processed from a unit of whole blood, then only a two-bag set is needed (one blood collection bag and one satellite bag for plasma). If a four-bag set is used to collect the whole blood in this situation, two of the satellite bags will go unused. Extra satellite bags unnecessarily increase cost and are wasteful. In addition, extra satellite bags are unwieldy and burdensome during blood collection, transportation from the remote collection site, and centrifugation. Extra satellite bags pose problems especially during centrifugation where all of the bags must fit within the centrifuge bucket, and be balanced, and positioned in the centrifuge so that none of the bags, tubes, or valves is damaged during high-speed centrifugation.

It is, therefore, highly desirable to collect whole blood without using extra satellite bags. This is hard to do because technicians who collect whole blood at the remote sites are in a poor position to determine what blood products will need to be processed from a given donor's blood and, as a result, what number of satellite bags are needed. With the advent of sterile docking, U.S. Pat. No. 4,507,119 and U.S. Pat. No. 4,443,215, it became possible to maintain a closed sterile system for blood processing without using a multiple bag system. Sterile docking devices, which are known in the art, connect originally unconnected bags and tubes under sterile conditions. However, even though sterile docking systems have been known to the art since the 1980's, techniques of sterile docking have not been used to improve the efficiency of whole blood collection and processing procedures as described here. It is one goal of this invention to use sterile docking to eliminate unnecessary satellite bags from blood collection systems.

When collecting blood components for transfusion, it is also desirable to minimize the presence of impurities or other materials that may cause side effects in the recipient. For example, to reduce the occurrence of alloimmunization and febrile transfusion reactions, it is desirable to remove substantially all of the leukocytes from whole blood prior to transfusion, storage or separation into its clinically therapeutic components.

In blood banks and hospitals, the most common way to remove leukocytes from whole blood is by using a leukocyte removal filter. Leukocyte removal filters and whole blood collection systems that use leukocyte removal filters are well known in the art. Kikugawa et al. in Vox Sang., Vol. 34, 281–290 (1975) describe cotton wool filters to remove leukocytes. Diepenhorst et al. in Vox Sang., Vol. 23, 308–320 (1972) and Vol. 29, 15–22 (1975) disclose using compressed air to force blood through a cotton wool filter in an open blood collection system. In closed systems using leukocyte removal filters (see U.S. Pat. Nos. 4,915,848; 4,919,823; and 5,104,788) filtration occurs after the blood has been separated into components and involves exposing only the red blood cell layer to the filter.

U.S. Pat. No. 4,985,153 discloses a leukocyte removal filter placed between the phlebotomy needle and the blood-collection bag with means to disconnect the filter after blood has been collected in the collection bag. Although an improvement over previous systems, that invention suffers the drawback of having the blood-collection bag be part of a multiple bag system. U.S. Pat. No. 5,092,996 describes sterile docking a filter to a single blood-collection bag, but in such a system the filtration occurs after the blood has already been collected in the blood-collection bag. It is advantageous to remove leukocytes from whole blood prior to collection in a single unattached blood-collection bag in order to allow for greater flexibility in subsequent blood processing steps.

SUMMARY OF THE INVENTION

One goal of this invention is to provide a system wherein the technician, without prior knowledge of blood product demand, can collect whole blood and the collected whole blood can be transported and processed with minimum waste and difficulty.

This invention provides a method for manufacturing blood products from whole blood comprising the steps of collecting whole blood, in blood-collection bags, from a plurality of donors, at one or more blood-collection sites, wherein said blood is collected by one or more technicians, and no determination is made at said one or more blood-collection sites as to what blood products are to be manufactured from said blood; marking said blood-collection bags with required information including time of collection; transporting filled blood-collection bags from said one or more blood-collection sites to a manufacturing site; compiling information at a site remote from at least one blood-collection site, preferably at said manufacturing site, regarding current demand for separate blood products which can be manufactured from the blood in said blood-collection bags; determining at a site remote from at least one blood-collection site, preferably at said manufacturing site, what blood products are to be manufactured from blood in said blood-collection bags; and separating said blood products from said blood. After separation, blood products may be further processed and stored.

"Whole blood" is blood as taken from a donor in its original, unseparated form.

The term "blood products" refers to the therapeutic components of blood, usually red blood cells, platelets, and plasma, which can be separated from whole blood and administered to patients.

The term "manufacturing blood products" means separating blood products from whole blood as is known to the art. The following components are routinely prepared from a unit (about 500 ml) of whole blood: packed red blood cells (RBC), plasma (either for transfusion or source plasma for fractionation), and platelets (platelet concentrates, also known as random donor platelet concentrates). Manufacturing such blood products as used herein refers to an industrial process in which multiple blood components are produced from blood taken from multiple donors, preferably at multiple remote locations, and supplied to multiple customers for use by multiple consumers. The process of this invention takes advantage of economies of scale such as those disclosed herein, including the economy of utilizing only one manager trained to make decisions regarding which blood products are to be separated from each bag of whole blood collected rather than requiring highly trained phlebotomists at the blood-collection sites to make such decisions.

Collecting whole blood is a procedure comprising removing blood from a blood donor. A needle is inserted into a donor's vein and the blood is allowed to drain (by gravity) through tubing into a collection bag. Preferably the collection bag contains anticoagulant to keep the blood from clotting. The blood collection system may also include pumps, vacuums, and scales to facilitate and monitor the process, all as known to the art.

Figure 1:
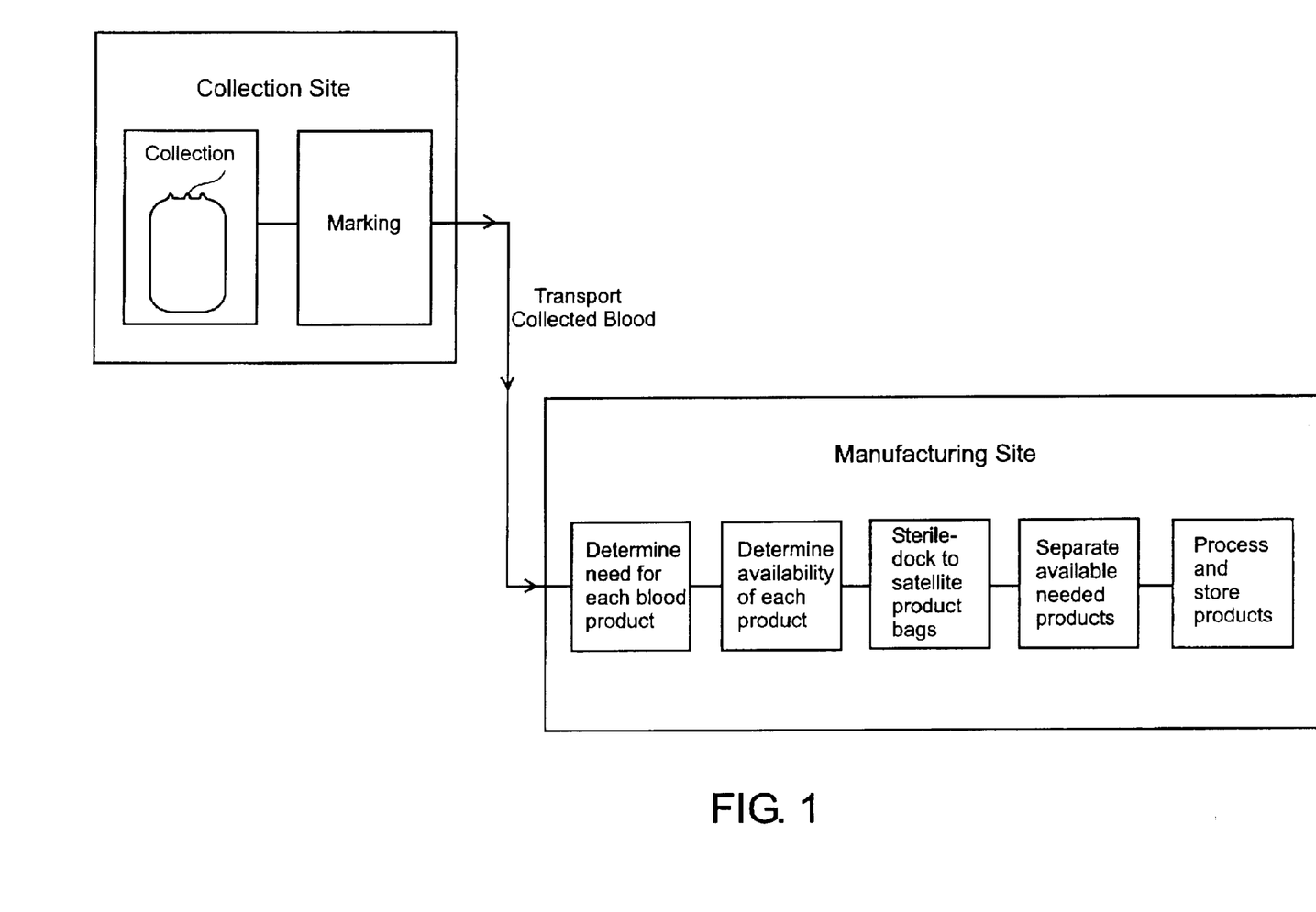
FIG. 1 is a flow diagram showing the method for manufacturing blood products from whole blood of this invention.

A blood-collection bag is any such bag used for receiving blood known to the art. Preferably, the blood collection bag is as shown in FIG. 1, without satellite bags attached at the time the blood is collected from the donor. Other blood-collection bags known to the art may also be used, such as those described in U.S. Pat. Nos. D440,300 S, D446,855 S, and 6,261,217. The blood collection bag may have only one tube connected thereto, or preferably no more than two; however, blood collection bags having additional tubes and inlets may also be used.

A "blood-collection bag" can be any bag used for collecting blood from a donor as known in the art. Blood collected in a blood-collection bag that is not attached to other bags is centrifuged to separate the blood into blood components. Then, the blood-collection bag is sterile docked to a number of satellite bags that corresponds to the number of blood products it has been determined to manufacture from the whole blood. Blood in a blood-collection bag may be processed, such as by centrifuging, in the blood-collection bag before separation into satellite bags, or the blood may be transferred (by gravity or by pumping) from the blood-collection bag to a blood-processing bag.

A "blood-processing bag" is any such bag known in the art, other than the blood-collection bag, used for processing blood. The blood-processing bag may be preconnected to the blood-collection bag or attached to the blood-collection bag through sterile docking. Blood transferred to a blood-processing bag is centrifuged. Prior to centrifuging or immediately after centrifuging, the blood-processing bag is sterile docked to a number of satellite bags that corresponds to the number of blood products it has been determined to manufacture from the whole blood.

Blood is typically collected by a technician, also called a "phlebotomist," who, in prior art methods, was required to select a multiple bag set comprising one, two, three, or more satellite blood product bags, depending on what blood products were to be separated from the blood. This requires special training of the phlebotomist to determine what blood products will be, or are likely to be, separated from a given bag of whole blood, and to collect the blood in the appropriate bag set. If the phlebotomist's determination was in error, either too many satellite bags would be used, resulting in waste of bags, or too few bags would be used, resulting in blood products which could have been collected not being collected.

In the method of this invention, once bags of whole blood have been transferred to the blood product manufacturing site, a trained manager, who is not present at the at least one blood-collection site, and is preferably present at the blood product manufacturing site, makes the decision as to which products should be separated from each bag of whole blood.

The blood-collection bag used for initial blood collection is preferably not connected to satellite blood bags at the time the blood is collected. Thereafter, at the blood product manufacturing site, satellite bags for receiving separated blood products can be connected via sterile docking to the blood collection bag, after the manager has made a determination as to what products are to be separated from the blood in the bag, so that the right number of satellite bags, one for each product to be separated, can be sterile docked to the blood-collection bag.

Alternatively, blood in the initial blood-collection bag may be transferred to a separate blood-processing bag, which is preconnected to appropriate satellite bags for receiving blood products. For example, it may be desirable to use a specially shaped blood-processing bag, such as a ring-shaped bag, compatible with some blood-separation equipment for blood processing. U.S. Pat. Nos. 6,315,706 and 6,348,031 disclose modified centrifuges using annular blood-processing bags attached to satellite bags for automatic separation and collection of blood components. The blood-collection bag may be preconnected to a blood-processing bag, such as a ring-shaped bag, with ensuing sterile docking of the blood-processing bag to satellite bags occurring at the blood-processing center. Attachment of the satellite bags to the blood-processing bag may be done prior to or after the time when blood is transferred from the initial blood-collection bag to the blood-processing bag.

The present invention also provides blood collection systems wherein whole blood is filtered through a leukocyte removal filter while being collected in a blood-collection bag that is not connected to other bags. "Leukocyte removal filter" means a device used to filter leukocytes from whole blood or a blood product while leaving other blood components intact, although platelets may also be removed if desired depending on the filter.

Currently available leukocyte removal filters employ various filtration media. One type of leukocyte removal filter contains a coarse pre-filter and a fine main filter made from non-woven, absorbent fibers. Commercially, a filter of this type is available from Asahi Medical under the trade name designation Sepacell™ RZ/RS. Another filter described in U.S. Pat. No. 4,925,572 contains three porous layers with successively smaller pore diameters.

A "blood collection system" comprises a phlebotomy needle, one or more tubes connecting the needle to a blood-collection bag, and may also comprise various features such as leukocyte removal filters, anticoagulant bags, scales, rockers, pumps, or a vacuum. Preferably, certain components of a blood collection system are disposable. Prior to use, the disposable blood collection system may be packaged in a suitable sterile pouch or bag.

One blood collection system of the present invention comprises a phlebotomy needle in fluid communication with one end of a first tube; the other end of the first tube being in fluid communication with the inlet of a leukocyte removal filter; a second tube in fluid communication with the outlet of the leukocyte removal filter; and the other end of the second tube being in fluid communication with a single blood-collection bag, said blood-collection bag not being connected to other bags. The blood-collection bag should have at least one, but no more than two, satellite tubes suitable for sterile docking with further system components. The blood-collection bag may contain anticoagulant or a bag containing anticoagulant may be connected to the first or second tube.

Means for sterile docking a blood-collection bag or a blood-processing bag to a further system component comprises at least one tube connected to the bag, other than the tube connected to the leukocyte removal filter or the phlebotomy needle, wherein the tube (the satellite tube) can be spliced to a further system component according to sterile docking methods and devices known in the art (see U.S. Pat. Nos.: 4,369,779; 4,412,835; 4,443,215; and 4,507,119). The tube used for sterile docking may be a tube on the blood-collection bag, such as the tube originally connected to the phlebotomy needle.

A "further system component" means a tube or bag other than the blood-collection bag, such as a blood-processing bag or a satellite bag (also called a blood-product bag), used for processing whole blood or collecting blood components.

A component of this invention is in "fluid communication" with another component when the two components are connected so that a fluid flowing through, into or from the first component will continue flowing through the second component.

In one embodiment of the invention, the blood collection system comprises a phlebotomy needle in fluid communication with one end of a first tube; the other end of the first tube being in fluid communication with a single blood-collection bag that is not connected to other bags; a pump in pumping relation to the first tube to assist in drawing blood from the donor into the blood-collection bag; a bag containing anticoagulant in fluid communication with a second tube; the second tube being in fluid communication with the first tube; and a second pump in pumping relation with the second tube to pump anticoagulant from the anticoagulant bag into the first tube.

The blood-collection bag may have one, and preferably no more than two, satellite tubes suitable for sterile docking with further system components. The tube used to fill the blood-collection bag may also or alternatively be used to connect to a satellite bag. Optionally, this system also includes a leukocyte removal filter connected to the first tube with another tube connecting the leukocyte removal filter to the blood-collection bag. The tube connected to the anticoagulant bag may connect with the first tube between the phlebotomy needle and a pressure sensor, see below, or between the first pump and the blood-collection bag.

"Pumping relation" with respect to the connection between a pump and a tube means that the pump is connected to a tube containing a fluid, such as whole blood, so that the pump forces the fluid through the tube. "Pumping relation" includes direct contact between the pump and the fluid, situations where a pump pushes the fluid through the tube by pumping a second liquid, such as anticoagulant solution, into the tube, and situations, such as with a peristaltic pump, where the pump compresses the tube and squeezes the fluid through the tube. Preferably, the pumps are peristaltic pumps with multiple rotor heads as known in the art.

The blood collection system of one embodiment of this invention may also include a pressure sensor comprising a pressure transducer positioned along the first tube between the phlebotomy needle and the first pump. The pressure transducer will produce an output signal corresponding to the pressure in the first tube. A controller receiving the output signal from the pressure transducer can adjust the speed of the first pump in response to the output signal. For example, if the pressure sensor detects low pressure in the first tube, the controller will increase the speed of the pump. The controller may also control the speed of the second pump in order to maintain a consistent ratio of anticoagulant to whole blood.

In another embodiment of this invention, a blood collection system comprises a phlebotomy needle in fluid communication with one end of a first tube; the other end of the first tube being in fluid communication with the inlet of a leukocyte removal filter; a second tube one end of which is in fluid communication with the outlet of the leukocyte reduction filter; the other end of the second tube being in fluid communication with a blood-collection bag containing anticoagulant, wherein the blood-collection bag is not connected to other bags; a sealable vacuum box for enclosing the blood-collection bag comprising a vacuum pump for evacuating the vacuum box and optionally, a scale inside the vacuum box capable of holding and weighing the blood-collection bag; wherein the flow rate of blood into the blood-collection bag can be varied by adjusting the vacuum. The blood-collection bag may have one, and preferably no more than two, satellite tubes suitable for sterile docking with further system components. Alternatively, the tube used to fill the blood-collection bag may be sterile-docked to a further system component.

This embodiment may alternatively add anticoagulant through a bag containing anticoagulant in fluid communication with either the first or second tube. The vacuum-assisted blood collection system described above may also comprise an oscillating shaker table supporting the vacuum box. The movements of the shaker table gently mix the anticoagulant in the blood-collection bag with the whole blood being collected.

A "blood component transferal system" comprises a blood-component bag containing centrifuged blood sterile docked to a tube connected to one or more satellite bags, wherein a pump or expresser forces the centrifuged blood into the satellite bags.

A "blood-component bag" is a blood-collection bag or a blood-processing bag containing blood that has been centrifuged, or otherwise processed, so that the blood components in the bag have separated into different layers located in separate regions of the bag.

Another embodiment of this invention is a blood component transferal system comprising a blood-component bag containing blood; wherein said blood has been centrifuged such that the blood components in the bag have separated into different layers located in separate regions of the bag; a tube with one end in fluid communication with the blood bag by sterile docking; the other end of the tube being split into at least two branches; at least two blood-product bags wherein each blood-product bag is in fluid communication with one of the branches; an optical controller comprising an optical sensor positioned to interrogate the tube upstream of where it splits into branches; wherein the optical sensor causes an output signal from the controller responsive to light received from fluid flowing through the tube; and a clamp on at least one of the branches capable of opening and closing in response to the output signal from the optical controller.

The blood component transferal system may also include a pump, preferably a peristaltic pump, in pumping relation to the tube to pump blood components from the blood-component bag to the blood product bags. As an alternative to the pump, an express or may be used. An expresser is a device containing two plates on opposite sides of the blood-component bag. "In pressing relation" means that the plates of the expresser are on opposite sides of the blood-component bag, such that when the plates are pressed against the blood bag toward each other, the fluid is forced out of the blood bag layer-by-layer into one or more appropriate satellite bags. If the blood was not filtered through a leukocyte removal filter, a leukocyte removal filter may be connected in fluid communication to the tube.

DETAILED DESCRIPTION OF THE INVENTION

As shown in FIG. 1, blood is collected at a collection site separate from the blood manufacturing site, such as a site at a distance requiring motorized transportation to reach, where the blood will be separated into desired blood products for ultimate use by patients. The collection site may be a satellite site such as a hospital donor center, a community donor center, a clinic, a temporary collection site, or a mobile blood collection site such as a van equipped with the proper equipment. The collection site may or may not have cold storage capacity for storing collected blood.

Preferably the blood is collected at the blood-collection site in a single collection bag that is not connected to other blood bags. Standard blood-collection bags are commercially available and allow collection of typical blood volumes of about 450 to about 500 ml of whole blood. Preferably the collection bag contains anticoagulant, e.g. about 63 ml of CPD, CP2D or CPDA-1 anticoagulant but the amount of anticoagulant used can be varied depending on the amount of blood collected. Typically, phlebotomists employed to collect blood in such blood-collection facilities are trained only in the techniques of drawing blood, and not in techniques of separation of blood products, or in analyzing demand for specific blood products or evaluating the feasibility of separating specific products from blood collected from particular donors. The method of this invention does not require phlebotomists at the blood-collection site to make decisions regarding what blood products will be separated from the whole blood collected. The phlebotomist is only required to collect the blood, to mark the blood bag with information as to the date and time collected and information as to the identity of the donor.

The whole blood in the collection bags, marked with identifying information, is then transported to the blood product manufacturing site. A record should be made of whether or not the blood was refrigerated prior to and/or during transportation, and the storage temperature.

The blood is typed and screened at the blood processing site using known sampling procedures. The sampling procedures are separate from the blood processing but can be done contemporaneously. Typing includes testing to determine whether the blood is type A, B, AB, O or Rh positive or negative. Screening involves testing with respect to one or more of the following: antibody detection for known and unexpected antigens, including alanine aminotransferase (ALT), Hepatitis B surface antigen, p24 Human immunodeficiency virus antigen, antigens indicative of syphilis, (HBsAg), Hepatitis C (HCV), anti-HIV (antibodies to HIV), and Human T-cell lymphotropic virus (HTLV) I or II.

A manager at the blood product manufacturing site collects information about current consumer demand for each eft blood product that can be separated from whole blood. Blood products include red blood cells, platelets, plasma, and white blood cells. Subsequently the plasma can be processed to make cryoprecipitate (a component containing Factor VIII, von Willerand's factor, fibrinogen, and Factor XIII). This information about current consumer demand may be available through a continuously updated computer database tracking current orders and/or supplies on hand, or may be manually compiled.

Since blood products cannot be used after varying periods of time for each product, referred to as the expiration times, the expiration times of blood products in blood product inventories must be taken into account. For example, fresh frozen plasma generally expires about one year after it is drawn if stored at −18 degrees C. or colder, and within 24 hours of being thawed. Cryoprecipitate prepared from plasma may also be stored frozen for up to one year. Packed red cells in can be kept at 1–6 degrees C. for 21 to 42 days. For instance, packed red cells with residual anticoagulant from the collection procedure, such as CPD, CP2d, ACDA, or CPDA can be stored for 21 days. Using storage or additive solutions as known to the art, such as AS-3, SAG-M, or MAPP, packed red cells can be stored to 42 days. Packed red cells can be frozen and stored at −65 degrees C. for up to ten years. Platelets can be stored at 20–24 degrees C. with continuous agitation for up to five days.

The manager also determines what blood products are available from each bag of collected whole blood using the blood type information marked on the bags, information regarding the time and date of collection, subsequent storage temperature, if any, transportation, storage temperature during transportation, current time, and separation capacity at the manufacturing facility. For example, if the whole blood has been improperly refrigerated after collecting, and more than about 8–24 hours has elapsed, the whole blood may be unusable for the particular collection product desired. The blood may then be disposed of or the separation plans may have to be altered for collection of an alternative product. If certain antibodies are found in the screening phase, such as HIV or Hepatatis B, the whole blood may be disposed of, or may be used only for separation of red blood cells. The plasma might also be separated for use as a reagent.

If it has been more than eight hours since the blood was collected, or if the blood was refrigerated at the collection site, platelets should not be collected.

If a specific blood product is both needed and available, the blood collection bag is sent to the separation facility for separation. The blood collection bag may be used as the blood-processing bag, or the blood-collection bag may be attached to a blood-processing bag before or after collection of the blood. Separation may be done by any means known to the art, such as a Sorvall centrifuge that spins multiple whole blood collection bags at once, each in a centrifuge bucket. Preferably, separation is done using an automated separation system such as the Gambro Orbisac® system. (See generally U.S. Pat. Nos. 6,315,706 and 6,348,031.) This system provides a centrifuge that receives an annular whole blood or blood-processing bag. Satellite blood bags may be attached (sterile docked) to the blood-processing bag by tubing, and are placed in a compartment on the centrifuge for collecting desired blood products. Satellite bags only for the products to be separated need be attached. Satellite bags may also be attached to the blood-processing bag after centrifuging, for example, when an expresser is used to transfer blood products that have been separated into layers within the blood-processing bag. The expresser squeezes each product in turn into the appropriate satellite bag.

The blood may be filtered for leukoreduction to remove white cells as herein described before, during or after separation. After the blood products (red blood cells, platelets and/or plasma) are separated, the separated products are sent for further processing if required, storage, and/or shipment to consumers.

Further processing includes performing procedures known to the art for storing the components, such as freezing of plasma, resting platelets for about one hour then placing on a rotator, addition of storage solutions, refrigerating or freezing red blood cells and deglycerolizing. Thereafter the blood products may be sent to consumers as needed.

Figure 2:
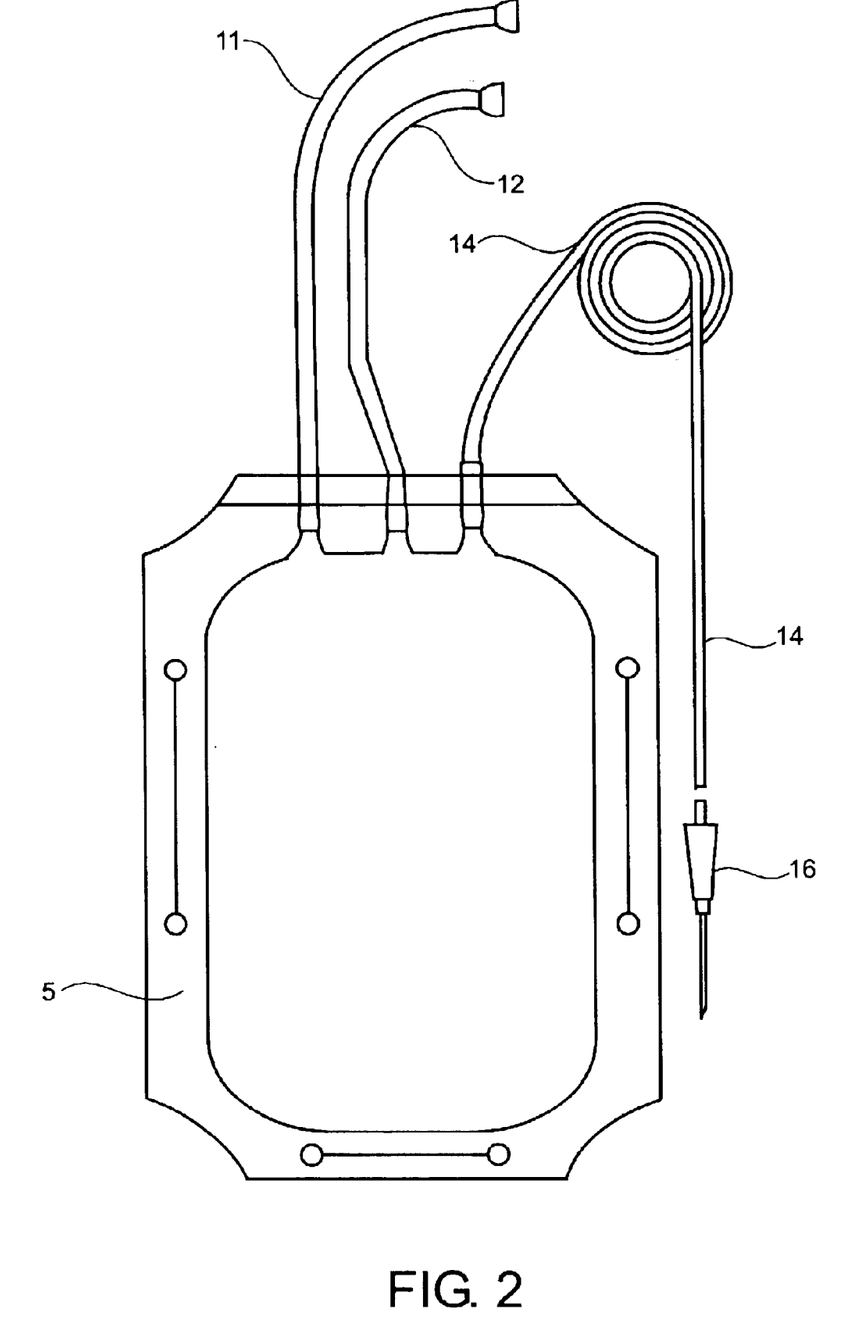
FIG. 2 shows a blood-collection bag of this invention.

FIG. 2 shows a blood-collection bag 5 of a whole blood collection system, said blood-collection bag 5 having one or more satellite tubes 11, 12 and needle line tube 14. A phlebotomy needle 16 attached to one end of needle line tube 14 is also shown. In FIG. 2, one or more satellite tubes 11 and 12 or needle line tube 14 can be used for sterile docking to further system components such as satellite bags (see bags 17 and 18 in FIG. 5. Blood-collection bag 5 may contain anticoagulant.

Figure 3:
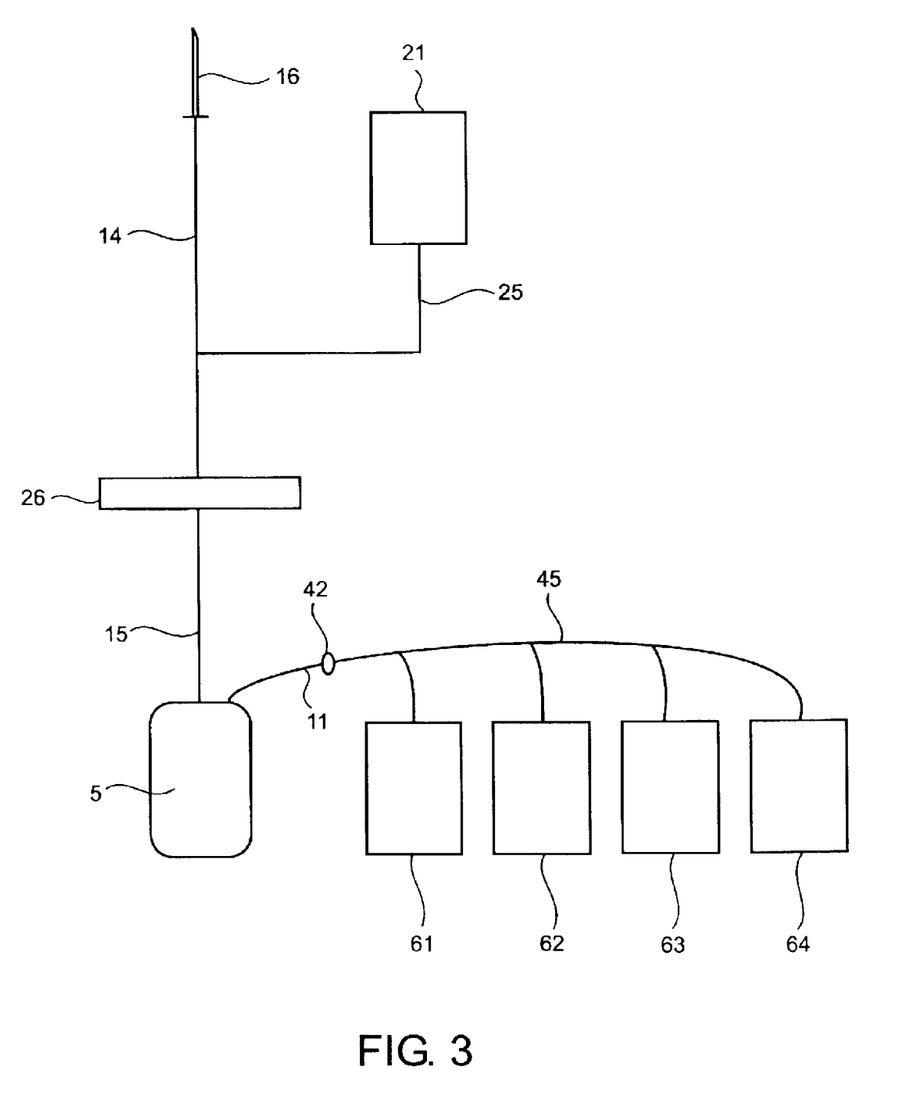
FIG. 3 is a schematic of a whole blood collection system having a leukocyte removal filter, an anticoagulant bag, and satellite blood product bags.

FIG. 3 shows a whole blood collection system. A phlebotomy needle 16 is attached to one end of needle line tube 14. The other end of needle line tube 14 is attached to the inlet of the leukocyte removal filter 26. One end of a bag line tube 15 is attached to the outlet of the leukocyte removal filter 26, and the other end of the bag line tube 15 is attached to the blood-collection bag 5. Leukocyte removal filter 26 may be a platelet filter (platelet sacrificing) also or alternatively, it may be platelet saving (or sparing) such that platelets will be allowed to pass the leukocyte removal filter 26. Anticoagulant bag 21, containing anticoagulant, is connected to one end of anticoagulant line 25. Anticoagulant can be pumped or the system may be configured so that it flows out of anticoagulant bag 21 by gravity. The other end of anticoagulant line 25 is connected to needle line tube 14. Although not shown in FIG. 3, anticoagulant line 25 may alternatively connect to bag line 15. Blood collection bag 5 may be connected to (sterile-docked) blood product satellite bags 61, 62, 63 and 64 via line 11 or bag line tube 15 may be disconnected from filter 26 and used for sterile docking of satellite bags. As shown in FIG. 3, line 11 is sterile-docked to satellite bag line 45 at docking point 42.

Also shown in FIG. 3 is a set of satellite bags sterile-docked to the blood collection system. One end of satellite tube 11 is connected in fluid communication to blood-collection bag 5. The other end of satellite tube 11 is sterile-docked to satellite bag line 45 at sterile docking point 42. Connected in fluid communication with satellite bag line 45 are satellite bags 61–64. A set of satellite bags will have at least one but no more than four satellite bags. Preferably an unattached blood-collection bag 5 will not be sterile-docked to a satellite bag set until after centrifuging.

Figure 4:
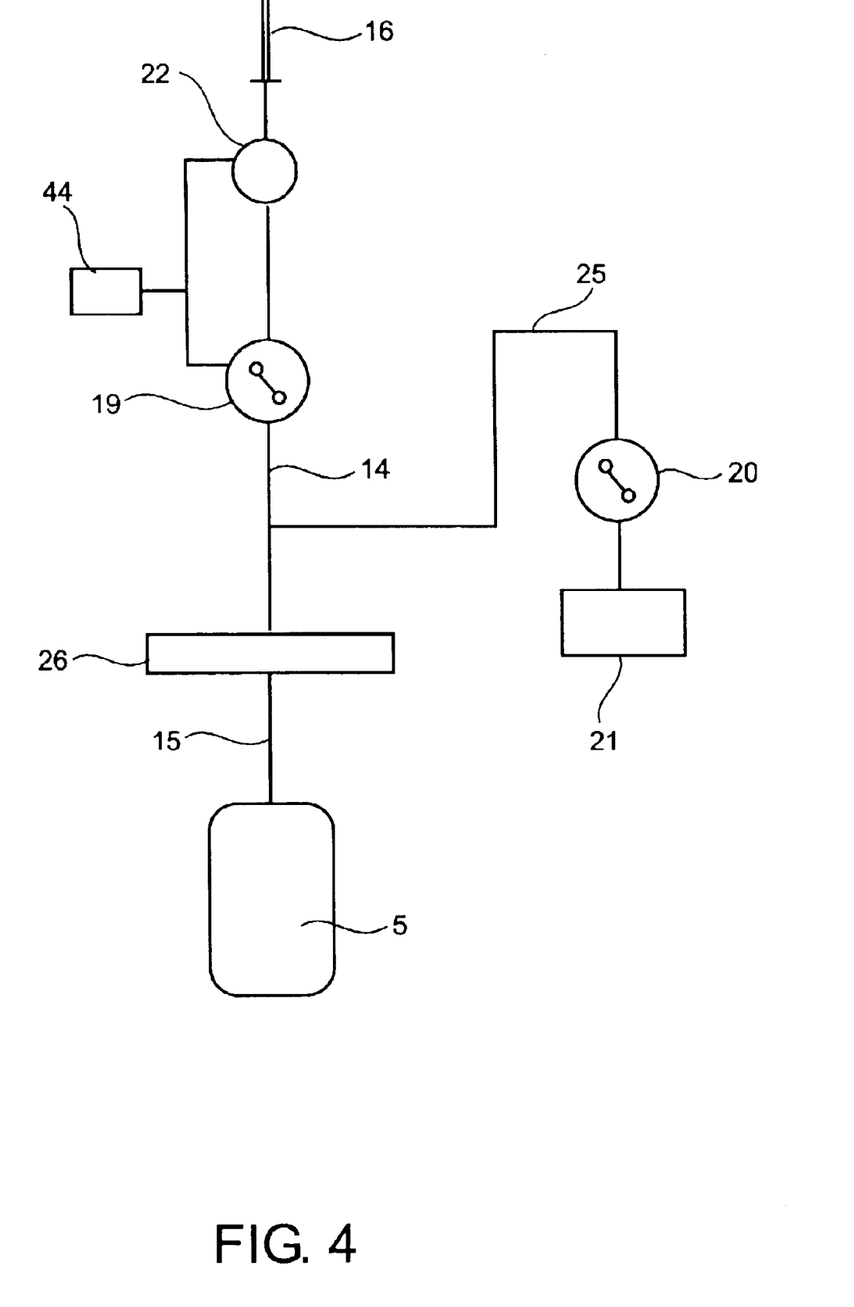
FIG. 4 is a schematic of a pump-assisted whole blood collection system further comprising means for pumping anticoagulant into the system according to another embodiment of the invention.

Shown in FIG. 4 is another embodiment of a whole blood collection system of the present invention. A phlebotomy needle 16 is attached to one end of needle line tube 14. The other end of needle line tube 14 is attached to the inlet of the leukocyte removal filter 26. One end of a bag line tube 15 is attached to the outlet of the leukocyte removal filter 26, and the other end of the bag line tube 15 is attached to the blood-collection bag 5. Also connected to needle line 14 is pump 19 and a pressure sensor 22. Pump 19 is used to assist in drawing blood from the donor into blood-collection bag 5 and is preferably a peristaltic pump.

Anticoagulant bag 21, containing anticoagulant, is connected to one end of anticoagulant line 25. The other end of anticoagulant line 25 is connected to needle line tube 14. Anticoagulant line 25 may also connect with needle line tube 14 between pump 19 and leukocyte removal filter 26, as shown in FIG. 4, or between needle 16 and pressure sensor 22. Connected to anticoagulant line 25 is a pump 20 for pumping anticoagulant from anticoagulant bag 21 into needle line tube 14. Pump 20 is preferably a peristaltic pump. The desired ratio of blood to anticoagulant in the blood being drawn from a donor by this system can be achieved by running pumps 19 and 20 at desirable relative speeds. Thus, simply changing the speed of one pump or the other pump can change the ratio of blood to anticoagulant.

Pressure sensor 22 has a pressure transducer that produces an output signal corresponding to the pressure of the fluid in needle line tube 14. Controller 44 is connected to pressure sensor 22 and pumps 19 and 20 and is capable of receiving the output signal from pressure sensor 22 and adjusting the speed of pumps 19 and 20 in response to the output signal. When the blood collection system shown in FIG. 4 is in operation, sensor 22 monitors the donor's pressure in needle line tube 14. Controller 44 monitors the output signals from sensor 22 and control the speed of pumps 19 and 20 in order to detect possible vein occlusions and/or maximize the blood and anticoagulant flow while keeping the pressure level at a value that ensures the donor's comfort.

Figure 5:
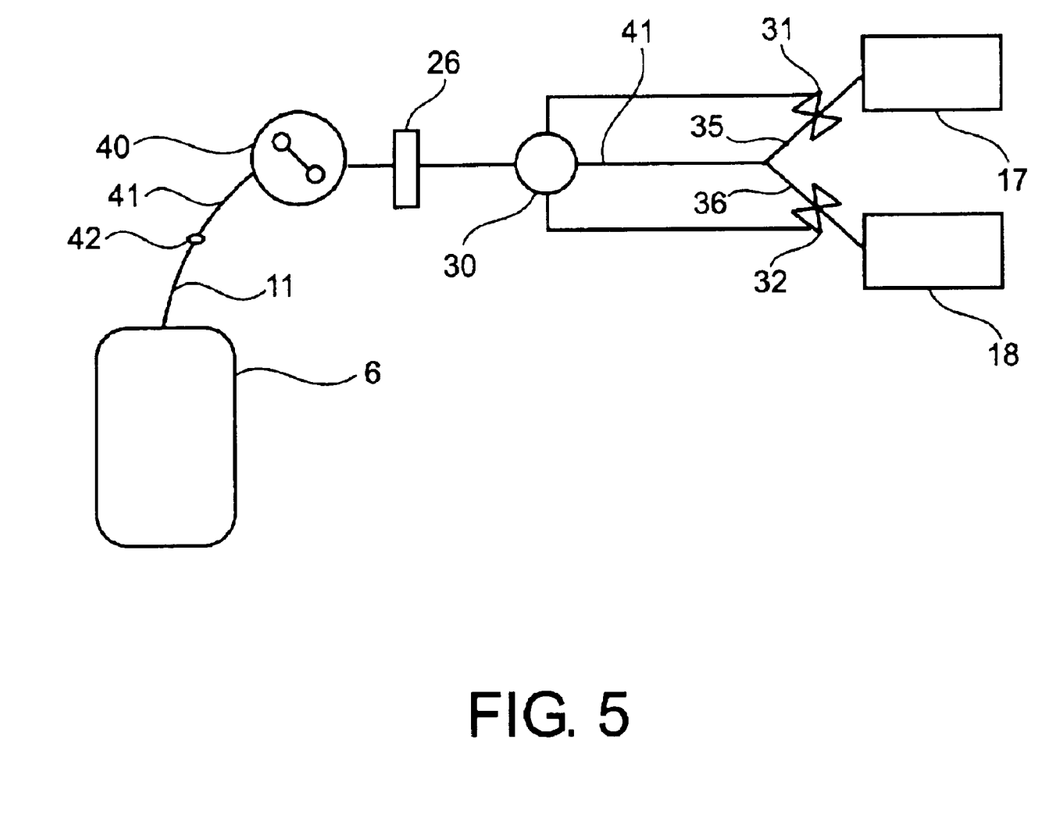
FIG. 5 is a schematic of a blood component transferal system using a pump.

A blood component transferal system may be sterile docked at the blood-processing center to a blood collection system before centrifuging or immediately after. As shown in FIG. 5, a blood component transferal system comprises a blood-component bag 6 containing anticoagulated blood separated into its separate component layers from centrifuging and one end of a satellite tube 11 connected to bag 6. The other end of satellite tube 11 is sterile docked at docking point 42 to transferal tube 41. Transferal tube 41 separates into at least two branches 35 and 36. The branches 35 and 36 connect to satellite bags 17 and 18. Connected to transferal tube 41 is a pump 40, preferably a peristaltic pump, for propelling the fluid from blood-component bag 6 to satellite bags 17 and 18. As an alternative to a pump 40, an expresser may be used to force the fluid out of blood-component bag 6. Also connected to transferal tube 41 is a controller 30 comprising an optical sensor for detecting the light received passing through the fluid in satellite tube 41. On one or more of the branches 35 and 36 are automatic clamps 31 and 32. Clamps 31 and 32 can open and close according to output signal from controller 30. For example, when the plasma layer, a clear pale yellow liquid, is pumped from blood-component bag 6 through satellite tube 11 and transferal tube 41, it is detected by the optical sensor in controller 30, and the output signal from the controller 30 will cause clamp 31 to open and clamp 32 to close, which causes the plasma to collect in satellite bag 17. When the red blood cell layer, a dark red and opaque layer, passes by optical sensor 30, the output signal from optical sensor 30 will cause clamp 31 to close and clamp 32 to open, which causes the red blood cell layer to collect in satellite bag 18.

Figure 6:
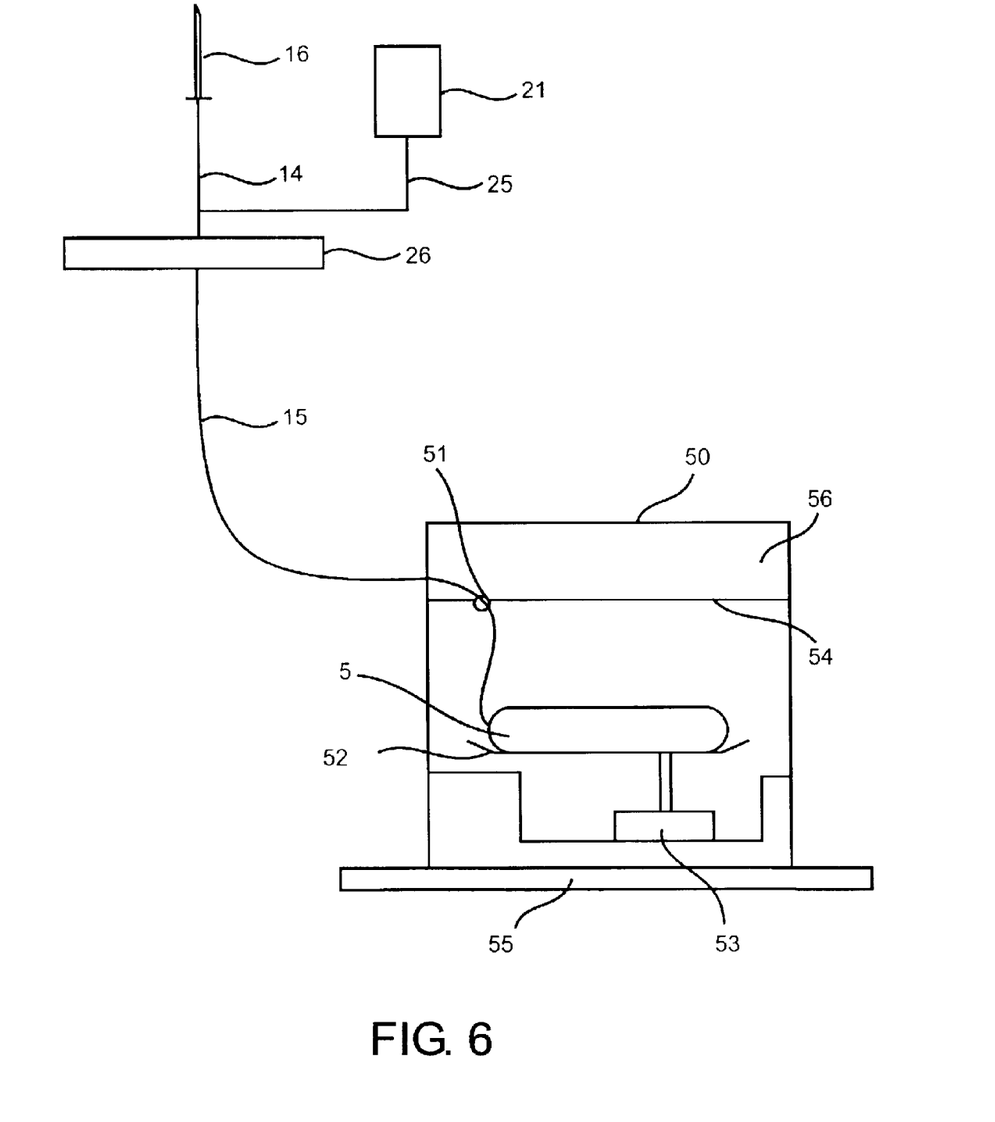
FIG. 6 is a schematic of a vacuum assisted whole blood collection system.

FIG. 6 shows another embodiment of the whole blood collection system of the present invention utilizing a vacuum to assist drawing blood from the donor into blood-collection bag 5. A phlebotomy needle 16 is attached to one end of needle line tube 14. The other end of needle line tube 14 is attached to the inlet of the leukocyte removal filter 26. One end of a bag line tube 15 is attached to the outlet of the leukocyte removal filter 26, and the other end of the bag line tube 15 is attached to the blood-collection bag 5. The blood-collection bag 5 is placed within vacuum box 50, supported on shaker table 55. Anticoagulant bag 21, containing anticoagulant, is connected to one end of anticoagulant line 25. The other end of anticoagulant line 25 is connected to needle line tube 14, as shown in FIG. 6. Although not shown in FIG. 6, anticoagulant line 25 may alternatively connect to bag line 15. Alternatively, blood-collection bag 5 may contain anticoagulant.

When the lid 56 of vacuum box 50 is closed, it will form an airtight seal 54. Vacuum box 50 also contains an opening 51 along where lid 56 fits on the rest of vacuum box 50. When the vacuum box 50 is closed, bag line tube 15 tightly fits through opening 51 maintaining continuity of seal 54. Within vacuum box 50 is a stand 52 capable of holding the blood-collection bag 5. Stand 52 is connected to scale 53 so that when an item, such as blood-collection bag 5, is placed on stand 52, scale 53 will measure and display the item's weight. Scale 53 may comprise a display visible through a window or transparent wall of vacuum box 50, or may transmit a signal to a display exterior to vacuum box 50. Vacuum box 50 contains a vacuum pump for evacuating vacuum box 50. By adjusting the vacuum, the blood flow into blood-collection bag 5 can be controlled.

Figure 7:
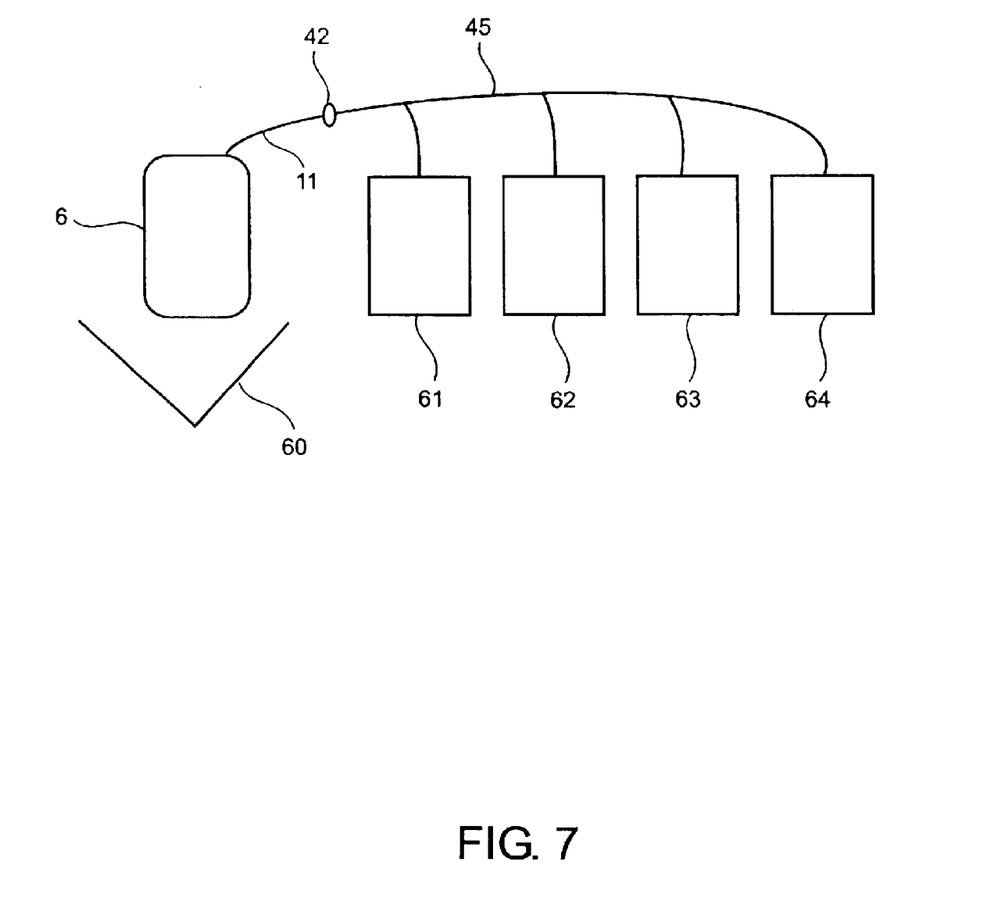
FIG. 7 is a schematic of a blood component transferal system using an expresser.

FIG. 7 shows a blood-component bag 6 sterile-docked to a satellite bag set. One end of satellite tube 11 is connected in fluid communication with blood-component bag 6. The other end of satellite tube 11 is sterile docked to satellite bag line 45 at sterile docking point 42. Connected in fluid communication with satellite bag line 45 are satellite bags 61–64. A set of satellite bags will have at least one but no more than four satellite bags. An expresser 60 is in pressing relation to blood-component bag 6 and can force the blood component layers out of blood-component bag 6 through tubes 11 and 45 and into satellite bags 61–64.

In order to operate a whole blood collection system, needle 16 of a blood collection system is inserted into a donor and gravity drainage is initiated, or the blood collection system may be installed on an apparatus having a vacuum box (see FIG. 6) or an apparatus having a pump 19 and/or sensor 22 (see FIG. 4) which is then turned on to activate the pump or vacuum box. A clamp, if used, may be released from tube 14, allowing blood to flow from the donor's arm along tube 14, whereupon it goes to bag 5 (FIG.

2) to mix with anticoagulant therein, or the blood mixes with anticoagulant at the connection of the anticoagulant tube 25 and tube 14 or 15 as shown in FIG. 4. The system is now collecting donor's blood. Pump 19, if used as shown in FIG. 4, is accelerated until the pump reaches a steady state that causes blood to flow along tube 14 to collection bag 5. This steady state is defined as the pump velocity when the pressure detected by sensor 22 falls within limits that provide for maximum flow with maximum donor comfort. If the pressure level remains normal, pump 19 will continue to draw blood and may be programmed to stop automatically when the collected volume of anticoagulated blood in bag 5 reaches the selected volume. The operator can manually stop the collection procedure at any time.

When collection is complete, tube 14 from needle 16 may be clamped, the needle 16 removed from the donor's arm, and a dressing applied at the puncture site. The anticoagulant tube 25 may be clamped downstream from pump 20 using a hemostat or other clamping device.

Collection bag 5 may then be centrifuged, or the collected blood may be transferred to a separate blood-processing bag. The blood-collection bag or blood-processing bag is provided with one or more further system components (e.g., satellite bags) to facilitate separation or processing of collected blood. For example, as shown in FIG. 5, blood-component bag 6 is sterile docked to a component pumping system containing the desired number of satellite bags needed for product collection. After centrifugation, blood-component bag 6 may contain anticoagulated blood separated into layered components, such as plasma and red blood cells. Then a conventional express or, as shown in FIG. 7, or a pump 40, which can be the same or different pump type as pump 19, is used to pump the separated components from blood-component bag 6 through tube 11. An optical sensor in controller 30 may be used to control clamps 31 and 32 to direct the separated components through branches 35 and 36 into satellite bags 17 and 18.

It will thus be seen that the objects set forth above, among those made apparent from the preceding description, are efficiently attained and, since certain changes may be made in the above sequence of steps and in the above construction without departing from the scope of the invention, it is intended that all matter in the above description or shown in the accompanying drawings shall be interpreted in an illustrative and not in a limiting sense. It is also understood that the following claims are intended to cover all of the generic and specific features of the invention described herein.

What is claimed is:

1. A method for making a blood collecting system comprising:
   providing a phlebotomy needle, first and second tubes, a leukocyte removal filter having an inlet and an outlet, a single blood-collection bag that is not connected to satellite bags for receiving separated blood products, and anticoagulant;
   connecting said needle to an end of said first tube;
   connecting another end of said first tube to the inlet of said filter;
   connecting the outlet of said filter to an end of the second tube;
   connecting another end of the second tube to said blood-collection bag; and
   placing said anticoagulant in said blood-collection bag before connecting said blood-collection bag to said second tube;
   wherein said method does not comprise connecting another bag to the fore-mentioned components.

2. A blood collection system comprising:
   a phlebotomy needle;
   a first tube in fluid communication with said needle;
   a first pump in pumping relation to the first tube;
   a sealable container containing a blood-collection bag in fluid communication with said first tube and a vacuum pump for controlling flow into said bag and structure for controlling flow into said bag, said blood-collection bag being a single bag that is not connected to any satellite bag for receiving separated blood products;
   an anticoagulant bag containing anticoagulant in fluid connection with a second tube, said second tube being in fluid communication with said first tube; and
   a second pump in pumping relation with said second tube for pumping anticoagulant into the first tube.

3. The system of claim 2 further comprising tubing for sterile docking said blood-collection bag to at least one further system component.

4. The system defined in claim 2 wherein each said pump is a peristaltic pump which includes a plurality of rollers.

5. The system defined in claim 2 further including a pressure transducer positioned between said phlebotomy needle and said first pump, said transducer producing an output signal corresponding to the pressure within said first tube.

6. The system defined in claim 5 further comprising a controller capable of receiving the output signal from said pressure transducer and adjusting the speed of said first pump in response to said output signal.

7. The system of claim 6 wherein said controller is also capable of controlling the speed of the second pump.

8. The system defined in claim 2 further comprising a whole blood leukocyte removal filter in fluid communication with said first tube.

9. The system defined in claim 2 wherein said second tube connects with said first tube between said phlebotomy needle and said pressure transducer.

10. The system defined in claim 2 wherein said second tube connects with said first tube between said first pump and said blood-collection bag.

11. A method of collecting blood comprising:
    activating a blood collection system of claim 2;
    inserting said phlebotomy needle into a patient's blood vessel; and
    collecting whole blood into said collection bag.

12. A method for making the system of claim 2 comprising:
    providing a phlebotomy needle, first and second tubes, a blood-collection bag that is not connected to other bags, first and second pumps, and an anticoagulant bag;
    connecting said needle to an end of said first tube;
    connecting said anticoagulant bag to an end of said second tube;
    connecting another end of the second tube to the first tube;
    connecting another end of the first tube to said blood collection bag;
    placing said first pump in pumping relation to said first tube; and
    placing said second pump in pumping relation to second tube.

13. A blood collection system comprising:
    a phlebotomy needle;
    a first tube in fluid communication with said needle;
    a whole blood leukocyte removal filter having an inlet in fluid communication with first tube;

a second tube in fluid communication with an outlet of said filter;

a blood-collection bag in fluid communication with said second tube, said blood collection bag being a single bag that is not connected to other bags;

a sealable vacuum box comprising a vacuum pump for evacuating said vacuum box, wherein said blood-collection bag is sealed within said vacuum box and the flow rate of blood into said blood-collection bag is controlled by adjusting the vacuum; and a scale able to weigh said blood-collection bag while said blood-collection bag is sealed inside said vacuum box.

14. The system of claim 13 further comprising means for sterile docking said blood-collection bag to at least one further system component.

15. The system defined in claim 13 further comprising an oscillating shaker table supporting said vacuum box.

16. The system defined in claim 13 further comprising an anticoagulant bag containing anticoagulant in fluid communication with either said first tube or said second tube.

17. The system defined in claim 13 further comprising the blood-collection bag containing anticoagulant.

18. A method of collecting blood comprising:

activating a blood collection system of claim 13;

inserting said phlebotomy needle into a patient's blood vessel; and collecting whole blood into said collection bag.

19. A method for making a blood collecting system comprising:

providing a phlebotomy needle, a first and second tube, a leukocyte removal filter, a blood-collection bag that is not connected to other bags, a vacuum box comprising a vacuum pump for evacuating said vacuum box, a scale, and anticoagulant;

connecting said needle to an end of said first tube;

connecting another end of said tube to the inlet of said filter;

connecting the outlet of said filter to an end of the second tube;

connecting another end of the second tube to said blood collection bag;

placing said blood-collection bag inside said vacuum box, sealing said vacuum box, evacuating said vacuum box and placing said blood-collection bag on top of said scale; and placing said anticoagulant in said blood-collection bag.

20. A blood collection system comprising:

a phlebotomy needle;

a first tube in fluid communication with said needle;

a first pump in pumping relation to said first tube;

a blood-collection bag containing whole blood or whole blood from which only leukocytes have been removed in fluid communication with said first tube, said blood-collection bag being a single bag that is not connected to any satellite bag for receiving separated blood products;

an anticoagulant bag containing anticoagulant in fluid connection with a second tube, said second tube being in fluid communication with said first tube;

a second pump in pumping relation with said second tube for pumping anticoagulant into the first tube said first and second pumps being upstream of said fluid communication of the first and second tubes.

* * * * *

UNITED STATES PATENT AND TRADEMARK OFFICE
CERTIFICATE OF CORRECTION

PATENT NO. : 6,994,790 B2 Page 1 of 1
DATED : February 7, 2006
INVENTOR(S) : Corbin, III et al.

It is certified that error appears in the above-identified patent and that said Letters Patent is hereby corrected as shown below:

<u>Column 13,</u>
Lines 48-67, delete.

Signed and Sealed this

Thirteenth Day of June, 2006

JON W. DUDAS
*Director of the United States Patent and Trademark Office*